United States Patent [19]

Holtkamp

[11] Plant 4,777

[45] Oct. 13, 1981

[54] AFRICAN VIOLET PLANT

[76] Inventor: Reinhold Holtkamp, Werther Strasse 112, D-4294 Isselburg, Fed. Rep. of Germany

[21] Appl. No.: 172,396

[22] Filed: Jul. 25, 1980

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet named South Carolina, particularly characterized by its vigorous growth habit; intensive green leaves; strong upright flower stems; large star-shaped white flowers, with wavy petal edges, and by its floriferous corolla, which is positioned well above the leaves.

1 Drawing Figure

The present invention comprises a new and distinct cultivar of African violet plant, botanically known as *Saintpaulia ionantha,* and hereinafter referred to by the cultivar name South Carolina.

The new cultivar was referred to during the breeding and selection process by the designation E 10/3, and is a product of a planned breeding program. The basic objective of the breeding program was to create a new African violet cultivar having pure white, non-dropping flowers star-shaped in form.

The new cultivar was originated from a cross made in a controlled breeding program in Isselburg, West Germany. The female, or seed parent was a cultivar designated b. 322/1, a white, slightly semi-double variety. The male, or pollen parent was a cultivar designated b. 288/11 white star.

The new cultivar South Carolina was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and are retained through successive generations of asexual reproduction.

South Carolina has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of South Carolina, which in combination distinguish this African violet as a new and distinct cultivar:

1. Very vigorous growth habit.
2. Intensive green, shiny leaves.
3. Strong upright flower stems, 5–7 in number, each carrying 8–12 flowers.
4. Large star-shaped flowers, pure white in color with occasional pink shading.
5. Slightly wavy petal edges.
6. The corolla is centrally positioned well above the foliage, with the flowers being long lasting and non-dropping.

The new cultivar is similar in certain respects to Maine, disclosed in U.S. Plant Pat. No. 4,350. South Carolina is principally distinguished from Maine by its more floriferous habit, its raised corolla, larger, relatively more intense green leaves, and by its absence of violet-blue at the centers of the flowers.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., and Royal Horticultural Color Chart (RHS), except where general colors of ordinary significance are referred to. Color values were taken under natural light conditions approximately mid-day in Isselburg, West Germany.

Botanical classification: *Saintpaulia ionantha,* Ramat. cv. South Carolina.

Parentage:

*Male parent.*—b. 288/11 white star.

*Female parent.*—b. 322/1 white, slightly semi-double.

Propagation: The new cultivar holds its distinguishing characteristics through successive propagations by leaf cuttings.

Plant: From 10 cm. to 13 cm. tall when grown in pots, and approximately 27–35 cm. in diameter when fully grown.

Leaves:

*General form.*—Heart-shaped.

*Diameter.*—70–80 mm.

*Texture.*—Firm, leathery, hairy.

*Aspect.*—Shiny.

*Veins.*—Upperside visible; underside well-pronounced, light green, shiny, slightly hairy.

*Color (upperside).*—HCC Spinach green 0960.

*Color (underside).*—HCC Lavender green 000761/3.

*Petiole.*—HCC Pod green 061/1.

Flowers:

*Buds.*—Bell-shaped, 9–11 mm. just before opening; 8–12 per stem.

*Sepals.*—Number varies; normally 5, occasionally 4 or 6. Color: Pod green 061. Calyx: Flat, funnel-shaped. Aspect: Spear-shaped. Peduncle: Peduncle of mature terminal flower bends down.

Individual flowers:

*Size.*—Between 40–45 mm. in diameter.

*Color.*—Upperside: RHS 155D, crystal-like; center slightly greenish; occasional pink shade on part of petal; right after opening young flower seems greenish-white. Underside: RHS 155D.

*Borne.*—Flower stem carries 7–12 flowers on short, strong peduncles; peduncle of mature terminal flower bends down.

*Shape.*—Star-shaped; 5–7 same size petals.

*Flowering time.*—6–7 weeks after parting first flowers appear; 8–10 weeks to full flowering saleable plant.

Reproductive organs:

*Anthers.*—5–6, composed of 10–12 cells, with seed capsule pushed slightly through; color Aurenlin/3.

*Filaments.*—4 mm. long; light green.

*Styles.*—7 mm.; light purple, base of ovary light green hairy.

*Pollen color.*—HCC Dresden yellow 64/2.

Roots: Well developed, white when young and active; brownish when older; strong main roots.

Disease resistance: Good as experienced to date.

General observations: South Carolina is a very vigorous grower with lush green and firm yet flexible leaves. The corolla stands well above the foliage. The large long-lasting, non-dropping star-shaped blossoms are supported by strong, wire-like stems.

I claim:

1. A new and distinct cultivar of African violet known by the cultivar name South Carolina, as described and illustrated, and particularly characterized by its vigorous growth habit; intensive green leaves; strong upright flower stems; large star-shaped white flowers, with wavy petal edges, and by its floriferous corolla, which is positioned well above the leaves.

* * * * *

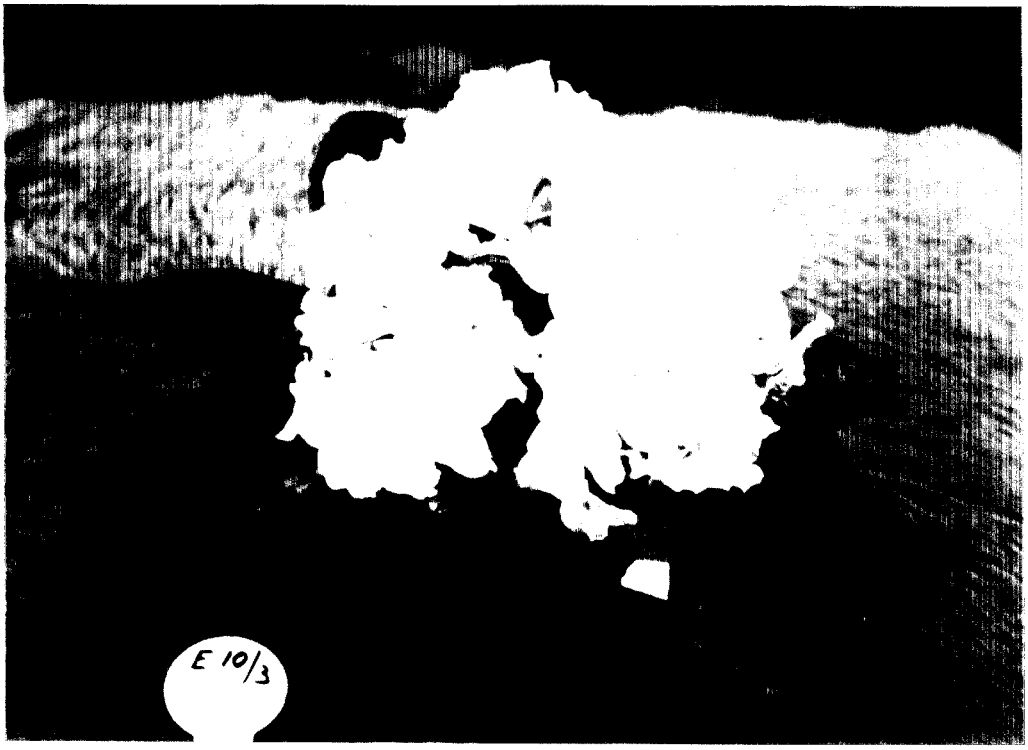
E 10/3